United States Patent [19]

Nedelec et al.

[11] 4,296,126

[45] Oct. 20, 1981

[54] 3-ARYLOXY-3-ARYL-PROPANEAMINES AND THEIR METHOD OF USE

[75] Inventors: Lucien Nedelec, Le Raincy; Daniel Fréchet, Paris; Claude Dumont, Nogent-sur-Marne, all of France

[73] Assignee: Roussel Uclaf, Paris, France

[21] Appl. No.: 13,831

[22] Filed: Feb. 22, 1979

[30] Foreign Application Priority Data

Feb. 24, 1978 [FR] France .................. 78 05335

[51] Int. Cl.³ .................. A01N 37/30; A61K 31/135; C07C 93/02

[52] U.S. Cl. ........................ 424/316; 260/501.18; 260/501.19; 424/330; 564/220; 564/346; 564/347; 564/355

[58] Field of Search ........... 260/570.6, 501.18, 501.19, 260/562 P; 424/316, 330; 564/346, 347

[56] References Cited

U.S. PATENT DOCUMENTS

| | | | |
|---|---|---|---|
| 2,683,742 | 7/1954 | Cusic | 260/570.6 X |
| 3,106,564 | 10/1963 | Fleming et al. | 260/570.6 X |
| 3,496,195 | 2/1970 | Ecsery et al. | 260/570.8 X |
| 4,018,895 | 4/1977 | Molloy et al. | 260/570.6 X |

Primary Examiner—Robert V. Hines

Attorney, Agent, or Firm—Hammond & Littell, Weissenberger and Muserlian

[57] ABSTRACT

Novel benzene-propanamines of the formula

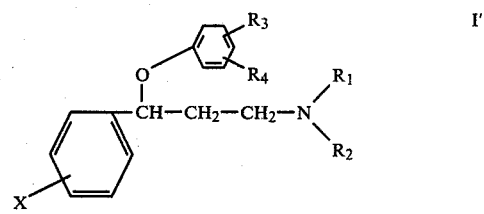

wherein X is selected from the group consisting of hydrogen, chlorine, fluorine and bromine, $R_1$ is selected from the group consisting of hydrogen and alkyl of 1 to 5 carbon atoms, $R_2$ is alkyl of 1 to 5 carbon atoms, $R_3$ is selected from the group consisting of hydrogen, chlorine, bromine, $-CF_3$, methyl and methoxy when $R_4$ is nitro and $R_3$ is selected from the group consisting of amino and acetamido when $R_4$ is hydrogen and their non-toxic, pharmaceutically acceptable acid addition salts having anorexigenic activity and inhibit serotonine uptake in vivo and in vitro and their preparation.

22 Claims, No Drawings

3-ARYLOXY-3-ARYL-PROPANEAMINES AND THEIR METHOD OF USE

STATE OF THE ART

Related prior art includes French Pat. Nos. 2,257,288 and 2,148,001.

OBJECTS OF THE INVENTION

It is an object of the invention to provide the novel benzene-propanamines of formula I' and their non-toxic, pharmaceutically acceptable acid addition salts and a process for their preparation.

It is another object of the invention to provide novel anorexigenic compositions and to provide a novel method of curbing the appetite of warm-blooded animals.

These and other objects and advantages of the invention will become obvious from the following detailed description.

THE INVENTION

The novel products of the invention are selected from the group consisting of benzene-propanamines of the formula

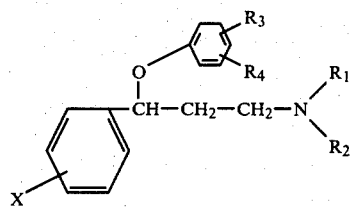

wherein X is selected from the group consisting of hydrogen, chlorine, fluorine and bromine, $R_1$ is selected from the group consisting of hydrogen and alkyl of 1 to 5 carbon atoms, $R_2$ is alkyl of 1 to 5 carbon atoms, $R_3$ is selected from the group consisting of hydrogen, chlorine, bromine, —$CF_3$, methyl and methoxy when $R_4$ is nitro and $R_3$ is selected from the group consisting of amino and acetamido when $R_4$ is hydrogen and their non-toxic, pharmaceutically acceptable acid addition salts.

A particularly preferred group of compounds of the invention are benzene-propanamines of the formula

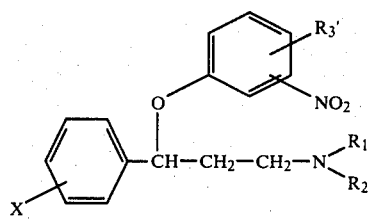

wherein X, $R_1$ and $R_2$ have the above definitions and $R_3'$ is selected from the group consisting of hydrogen, chlorine, bromine, —$CF_3$, methyl and methoxy and its non-toxic, pharmaceutically acceptable acid addition salts.

Examples of suitable alkyl groups of 1 to 5 carbon atoms for $R_1$ and $R_2$ are methyl, ethyl, propyl, isopropyl, butyl, isobutyl and pentyl. The benzene substituents may be in any position.

Examples of suitable acids for the non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, formic acid, benzoic acid, maleic acid, fumaric acid, succinic acid, tartaric acid, citric acid, oxalic acid, glyoxylic acid and aspartic acid, alkanesulfonic acids such as methanesulfonic acid and arylsulfonic acids such as benzene sulfonic acid.

Among the preferred compounds of formula I are those wherein X is hydrogen, those wherein X is hydrogen, $R_2$ is methyl and $R_1$ is methyl or hydrogen, those wherein X is hydrogen, $R_1$ and $R_2$ are methyl and $R_3'$ is hydrogen or —$CF_3$ and their non-toxic, pharmaceutically acceptable acid addition salts. Among the preferred compounds of formula I' are those wherein X is hydrogen or chlorine, $R_4$ is hydrogen and $R_3$ is amino or acetamido and those wherein X is hydrogen or chlorine, $R_4$ is hydrogen, $R_1$ and $R_2$ are methyl and $R_3$ is amino or acetamido and their non-toxic, pharmaceutically acceptable acid addition salts.

Preferred specific compounds of formula I' are N,N-dimethyl-γ-(4-nitrophenoxy)-benzene-propanamine oxalate, N,N-dimethyl-γ-(3-nitrophenxoy)-benzene-propanamine hydrochloride, N,N-dimethyl-γ-(2-nitrophenoxy)-benzene-propanamine fumarate, N,N-dimethyl-γ-(4-nitrophenoxy)-4-chloro-benzenepropanamine hydrochloride, N,N-dimethyl-γ-[4-nitro-3-trifluoromethyl-phenoxy]-4-chloro-benzene-propanamine oxalate, N,N-dimethyl-γ-(4-aminophenoxy)-benzene-propanamine and N-[4-(3-dimethylamino-1-phenyl-propyloxy)-phenyl]-acetamide oxalate.

The novel process of the invention for the preparation of a compound of formula I comprises reacting a compound of the formula

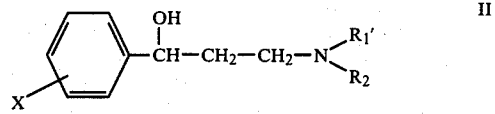

wherein X and $R_2$ have the above definition and $R_1'$ is alkyl of 1 to 5 carbon atoms with a compound of the formula

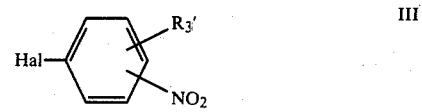

wherein Hal is chlorine, fluorine or bromine and $R_3'$ has the above definition to form a compound of the formula

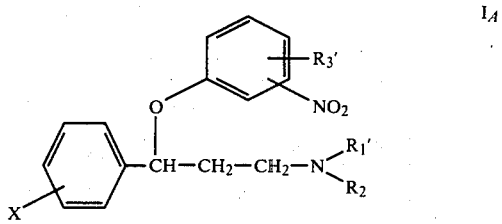

which may be isolated and, if desired, salified with an acid or desalkylated to obtain a compound of the formula

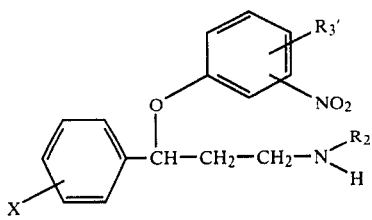

which may be isolated and salified, if desired, with an acid.

In a preferred embodiment of the invention, the reaction of the compounds of formulae II and III is effected in the presence of sodium hydride in a solvent such as tetrahydrofuran or dimethylformamide and most preferably dimethylsulfoxide. The desalkylation step is preferably effected with ethyl azodicarboxylate followed by acid hydrolysis.

The process of the invention for the preparation of compounds of formula I' wherein $R_3$ is acetamido or amino, $R_4$ is hydrogen and $R_1$ is alkyl of 1 to 5 carbon atoms comprises reacting a compound of formula II with a compound of the formula

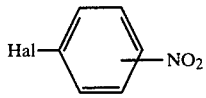

wherein Hal is chlorine, fluorine or bromine to obtain a compound of the formula

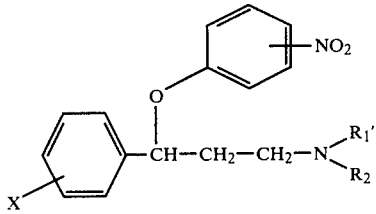

reducing the latter to obtain a compound of the formula

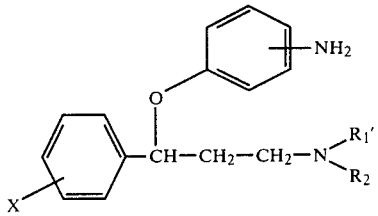

which may be isolated and, if desired, salified with an acid or reacted with an acetylation agent to obtain a compound of the formula

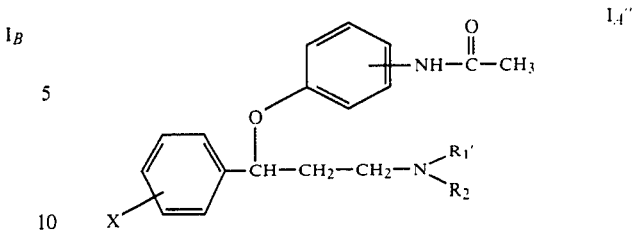

which may be isolated and, if desired, salified.

In a preferred mode of the said process, the reaction of the compounds of formulae II and III' is effected in the presence of sodium hydride in a solvent such as tetrahydrofuran or dimethylformamide or preferably dimethylsulfoxide. The reduction is preferably effected with hydrogen in the presence of platinum dioxide as the catalyst and the preferred acetylation agent is acetic acid anhydride.

The process of the invention for the preparation of the compounds of formula I' wherein $R_1$ and $R_2$ are hydrogen and $R_3$ is acetamido or $-NH_2$ comprises subjecting a compound of formula $IV_A$ to desalkylation to obtain a compound of the formula

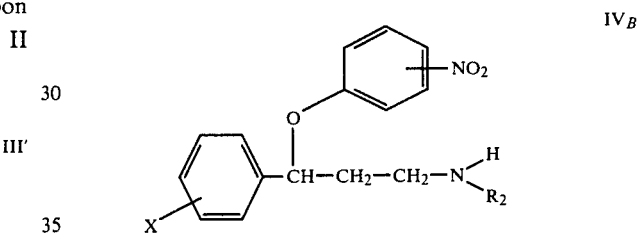

reducing the latter to form a compound of the formula

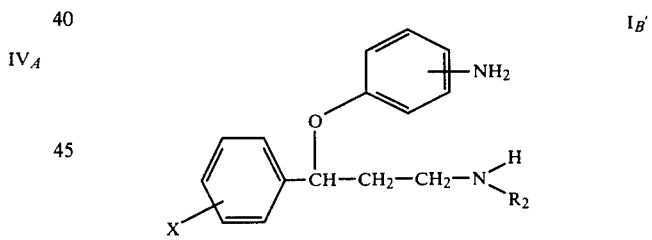

which may be isolated and if desired, salified with an acid or the compound of formula $I_A''$ may be desalkylated to obtain a compound of the formula

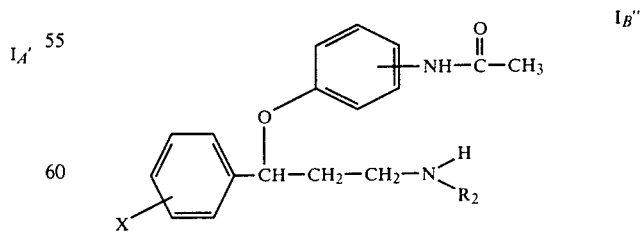

which may be isolated and, if desired, salified or hydrolyzed to obtain a compound of formula $I_B'$ which may be isolated and, if desired, salified.

The desalkylation may be effected with ethyl azodicarboxylate followed by acid hydrolysis and the reduction may be effected with hydrogen in the presence of a platinum dioxide catalyst.

The compound of formulae I and I' have a basic character and may be salified by reacting substantially stoichiometric proportions of the base and the desired acid.

The novel anorexigenic compositions of the invention are comprised of an anorexigenically effective amount of at least one compound of formula I' and its non-toxic, pharmaceutically acceptable acid addition salts and an inert pharmaceutical carrier or excipient. The compositions may be in the form of tablets, dragees, capsules, gelules, granules, suppositories and injectable solutions or suspensions.

Examples of suitable excipients are talc, gum arabic, lactose, starch, magnesium stearate, cocao butter, aqueous and nonaqueous vehicles, fatty bodies of animal or vegetable origin, paraffinic derivatives, glycols, diverse wetting agents, dispersants or emulsifiers and preservatives.

The compositions are useful for the treatment of simple or complicated obesity in adults or adolescents as well as in the treatment of depression, melancholy, manicdepressive psychoses, reactionary depression, exhaustion and neurotic depression since they also inhibit serotonine uptake.

Among the preferred compositions of the invention are those wherein X is hydrogen, those wherein X is hydrogen, $R_2$ is methyl and $R_1$ is methyl or hydrogen, those wherein X is hydrogen, $R_1$ and $R_2$ are methyl and $R_3'$ is hydrogen or —$CF_3$ and their non-toxic, pharmaceutically acceptable acid addition salts. Among other preferred compositions are those wherein X is hydrogen or chlorine, $R_4$ is hydrogen and $R_3$ is amino or acetamido and those wherein X is hydrogen or chlorine, $R_4$ is hydrogen, $R_1$ and $R_2$ are methyl and $R_3$ is amino or acetamido and their non-toxic, pharmaceutically acceptable acid addition salts.

Preferred specific compounds of formula I' are N,N-dimethyl-γ-(4-nitrophenoxy)-benzene-propanamine oxalate, N,N-dimethyl-γ-(3-nitrophenoxy)-benzene-propanamine hydrochloride, N,N-dimethyl-γ-(2-nitrophenoxy)-benzene-propanamine fumarate, N,N-dimethyl-γ-(4-nitrophenoxy)-4-chloro-benzene-propanamine hydrochloride, N,N-dimethyl-γ-[4-nitro-3-trifluoromethylphenoxy]-4-chloro-benzene-propanamine oxalate, N,N-dimethyl-γ-(4-aminophenoxy)-benzene-propanamine and N-[4-(3-dimethylamino-1-phenyl-propyloxy)-phenyl]-acetamide oxalate.

The novel method of curbing the appetite of warmblooded animals, including humans, comprises administering to warm-blooded animals an anorexigenically effective amount of at least one compound of formula I and its non-toxic, pharmaceutically acceptable acid addition salts. The compounds may be administered orally, rectally, or parenterally and the usual daily dose is 0.1 to 5 mg/kg depending upon the compound and method of administration.

The compounds of formula II which are not known may be prepared by the process of Ann. Chim., Vol. 51 (1961), p. 959.

In the following examples there are described several preferred embodiments to illustrate the invention. However, it should be understood that the invention is not intended to be limited to the specific embodiments.

EXAMPLE 1

N,N-dimethyl-γ-(4-nitrophenoxy)-benzene-propanamine oxalate 26 ml of dimethylsulfoxide were added to 2.6 g of a 50% dispersion of sodium hydride in oil and the mixture was stirred at 60°–65° C. for 30 minutes and was then cooled to 22° C. 5.8 g of N,N-dimethyl-3-phenyl-3-hydroxy-propanamine hydrochloride were added to the mixture which was then stirred for 10 minutes at 25° C. Then, 8.95 g of p-chloronitrobenzene were added to the mixture which was stirred at room temperature for 15 minutes. The mixture was extracted with methylene chloride and the organic phase was washed with water, dried, filtered and evaporated to dryness under reduced pressure to obtain 17 g of raw product. The latter was extracted 3 times with 200 ml of N hydrochloric acid and the neutral fraction was eliminated 3 times with 200 ml of ether. The combined aqueous phases were made alkaline with excess concentrated ammonium hydroxide and the precipitate was extracted with methylene chloride. The extract was dried, filtered and evaporated to dryness under reduced pressure to obtain 7.7 g of N,N-dimethyl-γ-(4-nitrophenoxy)benzene-propanamine.

The said product was dissolved in 25 ml of methanol and 3.28 g of oxalic acid were added thereto. The mixture was heated until dissolution occured and crystallization was induced. The mixture stood at room temperature for 2 hours and was vacuum filtered. The product was dried at 90° C. under reduced pressure to obtain 9.5 g of the oxalate of the said propanamine melting at 145° C. and then 150° C.

Analysis: $C_{19}H_{22}N_2O_7$; molecular weight=390.38.
Calculated: %C 58.45; %H 5.68; %N 7.18. Found: %C 58.5; %H 5.8; %N 7.0.

EXAMPLE 2

N,N-dimethyl-γ-(3-nitrophenoxy)-benzene-propanamine hydrochloride 57 ml of dimethylsulfoxide were added at 60°–65° C. to 5.7 g of a 50% oil-sodium hydride suspension and after cooling the mixture to 25° C., 10.55 g of N,N-dimethyl-3-phenyl-3-hydroxy-propanamine hydrochloride were added thereto under an inert atmosphere. The mixture stood at room temperature and 10.6 ml of 3-fluoro-nitrobenzene were added thereto. After standing at 25° C. for 18 hours, the mixture was extracted with methylene chloride and the organic phase was washed with water and evaporated to dryness under reduced pressure to obtain 25 g of raw product. The latter was extracted twice with 50 ml of N hydrochloric acid and the neutral fraction was extracted twice with 100 ml of ether. The aqueous phase was made alkaline with an excess of sodium hydroxide solution and was extracted with methylene chloride. The organic phase was washed with water and evaporated to dryness under reduced pressure to obtain 11 g of N,N-dimethyl-γ-(3-nitrophenoxy)-benzene-propanamine.

5.9 g of the said product were dissolved in 30 ml of ethyl acetate and an excess of gaseous hydrogen chloride in ethyl acetate was added thereto. The mixture was concentrated and crystallization was induced. The mixture was vacuum filtered and the recovered product was rinsed with ethyl acetate and dried to obtain 5.3 g of raw product which was crystallized from methanol to obtain 4.85 g of the hydrochloride of the said propanamine melting at 180° C. and then 185° C.

Analysis: $C_{17}H_{20}N_2O_3$. HCl; molecular weight=336.81. Calculated: %C 60.62; %H 6.29; %N 8.32; %Cl 10.53. Found: %C 60.9; %H 6.5; %N 8.1; %Cl 10.8.

EXAMPLE 3

N,N-dimethyl-γ-(2-nitro-phenoxy)-benzene-propanamine fumarate 70 ml of dimethylsulfoxide were added over 10 minutes at 60°–65° C. to a mixture of 20 ml of dimethylsulfoxide and 9.2 g of sodium hydride in a 50% oil disperson and after cooling the mixture to 25° C., 17.28 g of N,N-dimethyl-3-phenyl-3-hydroxy-propanamine were added thereto. The temperature returned to room temperature and 25.2 g of o-chloro-nitrobenzene were added thereto. The mixture was held at 25° C. for one hour and was then extracted with ethyl acetate. The organic phase was washed with water, dried and evaporated to dryness to obtain 41 g of raw product which was taken up twice in 100 ml of N hydrochloric acid. The neutral fraction was extracted twice with 400 ml of ether and the aqueous phase was made alkaline by addition of 50 ml of sodium hydroxide solution. The mixture was extracted with methylene chloride and the organic phase was washed with water, dried and treated with activated carbon. The mixture was filtered and the filtrate was evaporated to dryness to obtain 22 g of N,N-dimethyl-γ-(2-nitrophenoxy)-benzene-propanamine.

90 ml of ethyl acetate were added to a refluxing solution of 22 g of the said propanamine and 8.3 g of fumaric acid in 30 ml of methanol and the mixture was concentrated. Crystallization was induced and the mixture stood at 4° C. for a few hours after which it was vacuum filtered. The product was washed with ethyl acetate and was dried to obtain 17.45 g of the fumarate of the said propanamine melting at ≃115° C.

Analysis: $C_{17}H_{20}N_2O_3$. $C_4H_4O_4$: molecular weight=416.42. Calculated: %C 60.56; %H 5.81; %N 6.73. Found: %C 60.4; %H 5.9; %N 6.5.

EXAMPLE 4

N-methyl-γ-(2-nitrophenoxy)-benzene-propanamine oxalate 11.5 ml of ethyl azodicarboxylate were added at 20° C. under nitrogen to a solution of 11.5 g of N,N-dimethyl-γ-(2-nitrophenoxy)-benzene-propanamine in 120 ml of acetone and the mixture was refluxed for 18 hours. Reflux was interrupted for the addition of another 5.8 ml of ethyl azodicarboxylate and the mixture was refluxed for another 2 hours. The mixture was evaporated to dryness to obtain an oil which was added with stirring under nitrogen to 100 ml of N hydrochloric acid and the mixture stood at 20° C. for 25 hours. The neutral fraction was extracted twice with 300 ml of ether and the ether extracts were washed with 50 ml of N hydrochloric acid. The combined aqueous phases were made alkaline with sodium hydroxide solution and were then extracted with methylene chloride. The organic phase was washed with water, dried and evaporated to dryness to obtain 7.3 g of a brown oil. The latter was chromatographed over silica gel and was eluted with a 7-3 chloroform-methanol mixture to obtain 1.94 g of N-methyl-γ-(2-nitrophenoxy)-benzene-propanamine with an Rf=0.12.

1.94 g of the said product and 850 mg of oxalic acid were dissolved in 10 ml of refluxing methanol and 30 ml of ethyl acetate were added thereto. The mixture was concentrated and allowed to stand for a few hours at 4° C. The mixture was vacuum filtered and the recovered product was washed with ethyl acetate and dried at 60° C. under reduced pressure to obtain 1.8 g of the oxalate of the said propanamine melting at 133° C. and then 136° C.

Analysis: $C_{16}H_{18}N_2O_3$. $C_2H_2O_4$; molecular weight=376.36.

Calculated: %C 57.44; %H 5.35; %N 7.44. Found: %C 57.2; %H 5.4; %N 7.2.

EXAMPLE 5

N,N-dimethyl-γ-(4-nitrophenoxy)-4-chlorobenzene-propanamine hydrochloride 2.85 g of sodium hydride in a 50% oil suspension were added at 20° C. to a solution of 6.32 g of α-[2-dimethylamino-ethyl]-4-chlorobenzene methanol in 60 ml of dimethylformamide and 5.1 g of p-chloronitrobenzene were added thereto under nitrogen. The mixture was stirred for 45 minutes and 100 ml of water were added thereto at 25° C. The mixture was extracted with methylene chloride and the organic phase was washed with water, dried and evaporated to dryness to obtain 11.5 g of N,N-dimethyl-γ-(4-nitrophenoxy)-4-chlorobenzene-propanamine in the form of an orange oil.

The said oil was dissolved in 60 ml of ethyl acetate and gaseous hydrogen chloride in ethyl acetate was added thereto until the pH was acidic. The mixture stood in a refridgerator for 2 hours and was vacuum filtered. The recovered product was washed with ethyl acetate and dried at 80° C. under reduced pressure to obtain 9.65 g of the hydrochloride of the said propanamine melting at 190° C.

Analysis: $C_{17}H_{19}ClN_2O_3$. HCl; molecular weight=371.26. Calculated: %C 55.00; %H 5.43; %N 7.54; %Cl 19.10. Found: %C 54.8; %H 5.5; %N 7.3; %Cl 19.4.

EXAMPLE 6

N,N-dimethyl-γ-[4-nitro-3-trifluoromethyl-phenoxy]-4-chlorobenzene-propanamine oxalate 2.35 g of sodium hydride suspended in 50% oil and 30 ml of dimethylsulfoxide were added over 75 minutes to a solution of 7.50 g of α-[2-dimethylamino-ethyl]-4-chlorobenzene methanol in 60 ml of dimethylsulfoxide and the mixture was stirred for 2¼ hours. Then, 8.1 g of 5-chloro-2-nitro-trifluoromethyl-benzene and 32 ml of dimethylsulfoxide were added thereto and the mixture was stirred for 90 minutes. The mixture was cooled on an ice bath and was diluted with water. The mixture was extracted with ether and the ether phase was washed with water, dried over sodium sulfate and was evaporated to dryness to obtain 15 g of a brown liquid residue. The residue was chromatographed over silica gel and was eluted with a 6-3-1 benzene-ethyl acetate-triethanolamine mixture to obtain 5.1 g of N,N-dimethyl-γ-(4-nitro-3-trifluoromethyl-phenoxy)-4-chlorobenzene-propanamine.

The said product was taken up in 50 ml of ethanol and 1.6 g of oxalic acid dihydrate were added thereto. The mixture was warmed at 50° C. for 5 minutes and the temperature was cooled to room temperature. The mixture was iced for one hour and was vacuum filtered and the recovered product was washed and dried under reduced pressure. The product was taken up in ethanol and the solution was treated with activated carbon. The mixture was concentrated to start crystallization and was iced overnight and then was vacuum filtered. The recovered product was washed and dried to obtain 5 g of the oxalate of the said propanamine melting at 175° C.

Analysis: $C_{18}H_{18}ClF_3N_2O_3 \cdot C_2H_2O_4$; molecular weight=492.84. Calculated: %C 48.74; %H 4.09; %N 5.68; %Cl 7.19; %F 11.56. Found: %C 48.6; %H 4.2; %N 5.6; %Cl 7.2; %F 11.8.

EXAMPLE 7

N,N-dimethyl-γ-(4-aminophenoxy)benzene-propanamine 1.8 g of 82% platinum dioxide were added to a solution of 18.3 g of N,N-dimethyl-γ-(4-nitrophenoxy)benzene-propanamine in 200 ml of ethanol and the mixture was hydrogenated at 20° C. with stirring for 90 minutes. The mixture was filtered and the filtrate was evaporated to dryness to obtain 16.5 g of an orange oil which was crystallized from petroleum ether. The mixture was vacuum filtered and the product was washed and dried at 50° C. to obtain 14.9 g of N,N-dimethyl-γ-(4-aminophenoxy)-benzene-propanamine in the form of beige crystals melting at 77°-78° C.

Analysis: $C_{17}H_{22}N_2O$; molecular weight=270.36. Calculated: %C 75.52; %H 8.20; %N 10.36. Found: %C 75.3; %H 8.3; %N 10.2.

EXAMPLE 8

N-[4-(3-dimethylamino-1-phenyl-propyloxy)-phenyl]-acetamide oxalate 2.8 ml of 98% acetic acid anhydride were added under an inert atmosphere to a solution of 7.6 g of N,N-dimethyl-γ-(4-amino-phenoxy)-benzene-propanamine in 80 ml of benzene and the mixture was stirred for 45 minutes. 50 ml of 2 N sodium hydroxide were added thereto and the decanted organic phase was washed with aqueous sodium chloride solution and was dried, treated with activated carbon and filtered. The filtrate was evaporated to dryness to obtain 9 g of N-[4-(3-dimethylamino-1-phenyl-propyloxy)-phenyl]acetamide.

The said product and 3.5 g of oxalic acid dihydrate were dissolved in 25 ml of refluxing methanol and 75 ml of ethyl acetate were added thereto. The mixture was concentrated until crystallization started and was then held at 0° C. for 2 hours. The mixture was vacuum filtered and the product was washed and dried to obtain 11.4 g of the oxalate of the said acetamide melting at 106° C.

Analysis: $C_{19}H_{24}N_2O_2 \cdot C_2H_2O_4$; molecular weight=402.43. Calculated: %C 62.67; %H 6.51; %N 6.96. Found: %C 62.7; %H 6.9; %N 6.9.

EXAMPLE 9

Tablets were prepared containing 20 mg of N,N-dimethyl-γ-(4-nitrophenoxy)-benzene-propanamine oxalate and sufficient excipient of lactose, starch, talc and magnesium stearate for a final weight of 200 mg.

PHARMACOLOGICAL STUDY

Anorexigenic Activity in Dogs

The anorexigenic activity was studied in dogs using the method of Adams et al [J. Pharm. Sci., Vol. 53, (1964), p. 1405]. On the day of the test with the compound presumed to be anorexigenic, the individual daily ration of the animal was divided into about equal balls (10 to 20 g) which were offered to the dog every 10 minutes for 7 hours. Normally, the animal will regularly accept the successive balls when they are presented. Refusal shows anorexant activity of the test compound which was administered in lieu of the first ball. In this test, the compound of Example 1 showed anorexigenic activity at a dose of 3 mg/kg and grew with increasing doses.

Acute Toxicity

The $LD_{50}$ or lethal dose at which 50% of the animals died after intraperitoneal administration of the test compound to mice was determined 48 hours after the administration. The $LD_{50}$ for the compound of Example 1 was about 75 mg/kg.

Various modifications of the products and processes of the invention may be made without departing from the spirit or scope thereof and it is to be understood that the invention is intended to be limited only as defined in the appended claims.

We claim:

1. A compound selected from the group consisting of benzene-propanamines of the formula

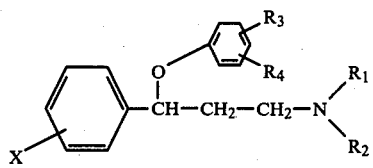

wherein X is selected from the group consisting of hydrogen, chlorine, fluorine and bromine, $R_1$ is selected from the group consisting of hydrogen and alkyl of 1 to 5 carbon atoms, $R_2$ is alkyl of 1 to 5 carbon atoms, $R_3$ is selected from the group consisting of hydrogen, chlorine, bromine, —CF$_3$, methyl and methoxy and $R_4$ is nitro and their non-toxic, pharmaceutically acceptable acid addition salts.

2. A compound of claim 1 wherein X is hydrogen.

3. A compound of claim 1 wherein X is hydrogen, $R_2$ is methyl and $R_1$ is selected from the group consisting of hydrogen and methyl.

4. A compound of claim 1 wherein X is hydrogen, $R_1$ and $R_2$ are methyl and $R_3$ is selected from the group consisting of hydrogen and —CF$_3$.

5. A compound of claim 1 which is N,N-dimethyl-γ-(4-nitrophenoxy)-benzene-propanamine oxalate.

6. A compound of claim 1 which is N,N-dimethyl-γ-(3-nitrophenoxy)-benzene-propanamine hydrochloride.

7. A compound of claim 1 which is N,N-dimethyl-γ-(2-nitrophenoxy)-benzene-propanamine fumarate.

8. A compound of claim 1 which is N,N-dimethyl-γ-(4-nitrophenoxy)-4-chloro-benzene-propanamine hydrochloride.

9. A compound of claim 1 which is N,N-dimethyl-γ-(4-nitro-3-trifluoromethyl-phenoxy)-4-chlorobenzene-propanamine oxalate.

10. An anorexigenic composition comprising an anorexigenically effective amount of at least one compound of claim 1 and an inert pharmaceutical carrier.

11. A composition of claim 10 wherein X is hydrogen.

12. A composition of claim 10 wherein X is hydrogen, $R_2$ is methyl and $R_1$ is selected from the group consisting of hydrogen and methyl.

13. A composition of claim 10 wherein X is hydrogen, $R_1$ and $R_2$ are methyl and $R_3$ is selected from the group consisting of hydrogen and —$CF_3$.

14. A method of curbing the appetite of warm-blooded animals comprising administering to warm-blooded animals an anorexigically effective amount of at least one compound of claim 1.

15. A method of claim 14 wherein X is hydrogen.

16. A method of claim 14 wherein X is hydrogen, $R_2$ is methyl and $R_1$ is selected from the group consisting of hydrogen and methyl.

17. A method of claim 14 wherein X is hydrogen, $R_1$ and $R_2$ are methyl and $R_3$ is selected from the group consisting of hydrogen and —$CF_3$.

18. A method of claim 14 which is N,N-dimethyl-γ-(4-nitrophenoxy)-benzene-propanamine oxalate.

19. A method of claim 14 wherein the compound is N,N-dimethyl-γ-(3-nitrophenoxy)-benzene-propanamine hydrochloride.

20. A method of claim 14 wherein the compound is N,N-dimethyl-γ-(2-nitrophenoxy)-benzene-propanamine fumarate.

21. A method of claim 14 wherein the compound is N,N-dimethyl-γ-(4-nitrophenoxy)-4-chloro-benzene-propanamine hydrochloride.

22. A method of claim 14 wherein the compound is N,N-dimethyl-γ-(4-nitro-3-trifluoromethyl-phenoxy)-4-chlorobenzene-propanamine oxalate.

* * * * *